US007585660B2

(12) United States Patent
Christensen et al.

(10) Patent No.: US 7,585,660 B2
(45) Date of Patent: Sep. 8, 2009

(54) GRASS ENDOPHYTES

(75) Inventors: Michael John Christensen, Palmerston North (NZ); Herrick Sydney Easton, Palmerston North (NZ); Lester Ronald Fletcher, Tai Tapu (NZ); Geoffrey Alexander Lane, Palmerston North (NZ); Garrick Cecil Morland Latch, Palmerston North (NZ); Lison Jean Popay, Hamilton (NZ); Brian Anthony Tapper, Palmerston North (NZ)

(73) Assignee: Grasslanz Technology Limited (NZ)

( * ) Notice: Subject to any disclaimer, the term of this patent is extended or adjusted under 35 U.S.C. 154(b) by 404 days.

(21) Appl. No.: 10/529,375

(22) PCT Filed: Sep. 26, 2003

(86) PCT No.: PCT/NZ03/00219

§ 371 (c)(1),
(2), (4) Date: Oct. 28, 2005

(87) PCT Pub. No.: WO2004/029227

PCT Pub. Date: Apr. 8, 2004

(65) Prior Publication Data

US 2006/0121593 A1 Jun. 8, 2006

(30) Foreign Application Priority Data

Sep. 27, 2002 (NZ) ..................... 521653

(51) Int. Cl.
*C12N 1/14* (2006.01)
(52) U.S. Cl. .................... 435/254.1; 424/93.5
(58) Field of Classification Search ............. None
See application file for complete search history.

(56) References Cited

U.S. PATENT DOCUMENTS 6,111,170 A 8/2000 Latch et al.
7,104,357 B2 * 9/2006 Baroni et al. ............... 181/121

FOREIGN PATENT DOCUMENTS

| JP | 2002-209441 | 7/2002 |
| WO | WO 00/40075 | 7/2000 |
| WO | WO 00/62600 | 10/2000 |
| WO | WO 02/13616 | 2/2002 |
| WO | WO 02/50572 A1 * | 6/2002 |

OTHER PUBLICATIONS http://animalscience.ag.utk.edu/pdf/Reports/nontoxic%20endophytes.pdf, accessed Dec. 4, 2007.*
West et al., Plant and Soil, 1988, vol. 112, pp. 3-6.*
Matthews et al., J. Anim. Sci. 2005. 83:1179-1185.*
Smith et al., Crop and Soil Environmental SCiences, 418-050 2002(http://www.ext.vt.edu/pubs/forage/418-050/418-050.pdf).*
Waller et al. (2000. Tall Fescues With Novel Endophytes in Tennessee. In: Proceedings of 4th International Neoptyphodium/Grass Interactions Symposium. Eds. V.H. Paul and P.D. Dapprich)).*
Bouton et al., Agronomy Journal, vol. 94, pp. 567-574 (2002).*
J.A. Parish et al., Use of Nonergot Alkaloid-Producing Endophytes for Alleviating Tall Fescue Toxicosis in Sheep[1,2], J. Anim. Sci. 81, pp. 1316-1322, (2003).
Blank, C.A.; Gwinn, K.D. 1992: Soilborne seedling diseases of tall fescue: influence of the endophyte Acremonium coenophialum. Phytopathology 82: 1089.
Bouton, J.H. 2000: The use of endophyte fungi for pasture improvement in the USA. In Proceedings of the Grassland Conference 2000, 4th International Neotyphodium/Grass Interactions Symposium. Eds. Paul, V.H.; Dapprich, P.D. Universtät, Paderborn, pp. 163-168.
Bouton, J.H.; Latch, G.C.M.; Hill, N.S.; Hoveland, C.S.; McCann, M.A.; Watson, R.H.; Parish, J.H.; Hawkins, L.L.; Thompson, F.N. 2002: Re-infection of tall fescue cultivars with non-ergot alkaloid-producing endophytes. Agronomy Journal 94: 567-574.
Elberson, H.W.; West, C.P. 1996: Growth and water relations of field grown tall fescue as influenced by drought and endophyte. Grass and Forage Science 51:333-342.
Fletcher, L.R.; Easton, H.S.; 2000: Using Endophytes for Pasture Improvement in New Zealand. In Proceedings of The Grassland Conference 2000, 4th International Neotyphodium/Grass Interactions Symposium. Eds. Paul, V.H.; Dapprich, P.D. Universtät, Paderborn, pp. 149-162.
Fletcher, L.R.; Sutherland, B.L.; Fletcher, C.G. 1999: The impact of endophyte on the health and productivity of sheep grazing ryegrass-based pastures. In Ryegrass endophyte: an essential New Zealnd symbiosis. Grassland Research and Practice Series No. 7, pp. 11-17.
Gadberry, M:.S.; Denard, T.M.; Spiers, D.E.; Piper, E.L. 1997: Ovis airies: A model for studying the effects of fescue toxins on animal performance in a heat-stressed environment. In Neotyphodium/Grass Interactions, Eds. Bacon, C.W.; Hill, N.S. Plenum Press, New York, pp. 429-431.
Griffiths, A.; Moon, C.; Tapper, B.; Christensen, M. 1999: Non-radioactive AFLP fingerprinting for detection of genetic variation in Epichloë/Neotyphodium endophytes. Proceedings of the 11th Australian Plant Breeding Conference.
Hill, N.S.; Thompson, F.N.; Studemann, J.A.; Rottinghaus, G.W.; Ju, H.J.; Dawe, D.L.; Hiatt, E.E. 2001: Ergot alkaloid transport across ruminant gastric tissues. Journal of Animal Science 79: 542-549.
Kren, V. 1999: Biotransformations of ergot alkaloids. In Ergot the genus *Claviceps*. Eds. Kren, V.; Cvak, L. Harwood Academic, Amsterdam, p. 230.
Latch, G.C.M.; Christensen, M.J. 1985: Artificial infection of grasses with endophytes. Annals of Applied Biology 107: 17-24.
Leuchtmann, A. 1997: Ecological diversity in Neotyphodium-infected grasses as influenced by host and fungus characteristics. In Neotyphodium/Grass Interactions, Eds. Bacon, C.W.; Hill, N.S. Plenum Press, New York, pp. 93-108.

(Continued)

*Primary Examiner*—Irene Marx
(74) *Attorney, Agent, or Firm*—Finnegan, Henderson, Farabow, Garrett & Dunner LLP

(57) ABSTRACT

The present invention relates to a combination of a *Neotyphodium* species endophyte or endophyte culture in a symbiotic association with a host grass which association does not cause symptoms of toxicosis in animals through exclusion of ergovaline but, due to the inclusion of alkaloids including agroclavine, setoclavine or isosetoclavine, retains the ability to resist abiotic stresses and protect the grass from pests.

8 Claims, No Drawings

OTHER PUBLICATIONS

Moon, C.D.; Tapper, B.A.; Scott, D.B. 1999: Identification of Epichloë endophytes in planta by a microsatellite-based PCR fingerprinting assay with automated analysis. Applied and Environmental Microbiology 65: 1268-1279.

Oliver, J.W. 1997: Physiological manifestations of endophyte toxicosis in ruminant and laboratory species. In Neotyphodium/Grass Interactions, Eds. Bacon, C.W.; Hill, N.S. Plenum Press, New York, pp. 311-346.

Rottinghaus, G.E.; G.B.; Cornell; C.N.; Ellis; J.L. 1991: HPLC method of quantitating ergovaline in endophyte-infected tall fescue; Seasonal variation of ergovaline levels in stems with leaf sheaths, leaf blades and seed heads. Journal of Agricultural and Food Chemistry 191: 112-115.

Rowan, D.D.; Hunt, M.B.; Gaynor, D.L. 1986: Peramine, a novel insect feeding deterrent from ryegrass infected with the endophyte *Acremonium loliae*. J. Chem. Soc. Chem. Commun. 1986. 935-936.

Rowan, D.D.; Latch, G.C.M. 1994: Utilization of endophyte-infected perennial ryegrasses for increased insect resistance. In Biotechnology of endophyte fungi in grasses. Eds. Bacon, C.W. White, J. CRC Press, pp. 169-183.

Siegel, M.R.; Latch, G.C.M.; Bush, L.P.; Fannin, F.F.; Rowan, D.D.; Tapper, B.A.; Bacon, C.W.; Johnson, M.C. 1990: Fungal endophyte-infected grasses: alkaloid accumulation and aphid response. Journal of Chemical Ecology 16: 3301-3315.

Stuedemann, J.A.; Hoveland. C. 1988: Fescue endophyte: History and impact on animal agriculture. Journal of Production Agriculture 1: 39-44.

Tapper, B.A.; Latch G.C.M. 1999: Selection against toxin production in endophyte-infected perennial ryegrass. In Ryegrass endophyte: an essential New Zealand symbiosis. Grassland Research and Practice Series No. 7, pp. 107-111.

Tor-Agbidye, J.; Blythe, L.L.; Craig, A.M. 2001: Correlation of endophyte toxins (ergovaline and lilitrem B) with clinical disease: fescue foot and perennial ryegrass staggers. Veterinary and Human Toxicology 43: 140-146.

Tsai, H.F.; Liu, J.S.; Staben, C.; Christensen, M.J.; Latch, G.C.; Siegel, M.R.; Schardl, C.L. 1994: Evolutionary diversification of fungal endophytes of tall fescue grass by hybridization with Epichloë species. Proceedings of the National Academy of Science USA 91: 2542-2546.

Yates, S.G.; Petroski, R.J.; Powell, R.G. 1990: Analysis of loline alkaloids in endophyte-infected tall fescue by capillary gas chromatography. Journal of Agricultural and Food Chemistry 38: 182-185.

Adcock R. A. et al., 1997: Symbiont regulation and reducing ergot alkaloid concentration by breeding endophyte-infected tall fescue. J. Chem. Ecology 23(3): 691-704.

International Search Report for PCT/NZ03/00219.

Joost R.E. 1995: Acremonium in Fescue and Ryegrass Boon or Brane? A review. J. Anim. Sci. 73: 881-888.

Roberts C. A. et al., 2002: Use of rat model to evaluate tall fescue seed infected with introduced strains of *Neotyphodium coenophialum*. J. Agric. Food. Chem. 50: 5742-5745.

Schardl C.L. et al., 2001: The gene for the determinant step in ergot alkaloid synthesis by *Neotyphodium coenophialum* and other grass endophytes. Phytopathology 91(6): S123.

* cited by examiner

GRASS ENDOPHYTES

TECHNICAL FIELD

This invention relates to fungal endophytes and combinations of endophytes with grass plants. More particularly the invention relates to endophytes which form combinations with tall fescue (*Festuca arundinacea*) and some other related grasses. Even more particularly the invention relates to combinations having reduced toxicity to grazing livestock as compared to cultivars of endophyte/tall fescue combinations in common use.

BACKGROUND ART

Fungal endophytes of the genus *Neotyphodium* (formerly *Acremonium*) infect a number of temperate climate Pooideae grasses. The *Neotyphodium* endophytes can produce alkaloids which are considered to confer degrees of pest and possibly disease protection upon the plants in which they naturally occur (Rowan and Latch, 1994; Blank and Gwinn, 1992). The *Neotyphodium* endophytes are vertically transmitted through the seed of the grasses and no natural horizontal transmission has been established (Leuchtmann,1997).

Many of the predominating natural endophyte infections of improved grass cultivars used for pastoral agriculture production also cause significant animal disorders, for example tall fescue toxicoses (Stuedemann and Hoveland, 1988) and ryegrass staggers (Fletcher et al., 1999). These may be complex toxic reactions by animals to alkaloids produced under a range of plant growth conditions. Significant economic loss within pastoral agriculture systems can occur due to such animal toxicoses. On the other hand presence of at least some endophytes may be essential for the competitive persistence of the chosen grass in a pasture (Elberson and West, 1996; Fletcher and Easton, 2000).

Grass lines can be artificially infected with selected endophytes. Axenic cultures of endophytes can be used to infect grass seedlings, grown initially under sterile conditions (Latch and Christensen, 1985), which are then selected for desirable qualifies, and multiplied for commercial use. Three significant examples of this technology have been developed by the Grasslands division of AgResearch Ltd: GREENSTONE™ tetraploid hybrid ryegrass with ENDOSAFE™ endophyte (Tapper and Latch, 1999, NZ Patent 233083); various perennial and hybrid ryegrasses with AR1 endophyte (Fletcher and Easton, 2000); and tall fescue cultivars with MaxQ™ endophyte (Bouton, 2000; Bouton et al., 2002, U.S. Pat. No. 6,111,170).

Fescue Toxicosis

Fescue toxicosis has been associated with the natural infection of tall fescue by common strains of *Neotyphodium coenophialum*. These strains typically produce the ergopeptine alkaloid, ergovaline, which is of a class of ergopeptines known to be toxic to mammals. Ergovaline is considered to be the primary cause of fescue toxicity. Other compounds, notably other ergoline and ergolene compounds, for example lysergic acid, possibly add to the syndrome (Oliver, 1997; Gadberry et al., 1997; Hill et al., 2001).

The ergovaline levels tend to be higher in leaf sheath and heads of tall fescue than in leaf blade and undergo seasonal variation (Rottinghaus et al., 1991). There is very little ergovaline in roots. Typically a concentration of ergovaline in herbage or herbage products such as hay, straw, seed or silage of greater than an average of 0.4 ppm of dry matter has been considered a risk of causing fescue toxicosis (Tor-Agbidye et al., 2001) especially when combined with climatic conditions exacerbating fescue toxicosis symptoms.

Other Compounds Recognised as Plant Defence Mechanisms—Peramine, Lolines

Peramine is produced in endophyte-infected grass (Rowan et al., 1986) and probably mobilised within the plant. It is a potent feeding deterrent for a range of insects, e.g. Argentine stem weevil (*Listronotus bonariensis*), (Rowan and Latch 1994) and a significant factor for protecting endophyte-infected grasses from insect pest predation.

Lolines (N-formylloline, N-acetylloline, N-acetyinorloline and other closely related compounds) are produced by some *Neotyphodium* endophytes including *N. coenophialum* typical of tall fescue. These compounds in appropriate endophyte-infected grasses have properties of deterring or resisting a number of insects, notably sucking insects, for example, *Rhopalosiphum padi* (Seigel et al., 1990).

Protective Effects in Tall Fescue Pastures—Persistence under Stress Conditions

Endophyte infection has been associated with enhanced persistence of tall fescue plants under water deficit or drought conditions. Whether this effect is due to better resistance of biotic stress factors expressed in water deficit situations; general better health of endophyte-infected tall fescue plants (particularly of root systems); or due to specific differential physiological responses of the endophyte-infected plants to water stress; is not clearly evident. However, the overall effect is enhanced resistance to water deficit.

Tremorgens

Some *Neotyphodium* endophytes, notably those of evolutionary derivation from strains of *Epichloë festucae* such as *N. lollii*, produce potent tremorgens which are toxic to grazing animals. To ensure such tremorgens are not produced by an endophyte artificially introduced into forage tall fescue or ryegrass, the presence of the known potent tremorgens typical of endophytes, that is the lolitrems, is tested for. Also tremorgenic activity in grazing test animals is looked for.

It is an object of the present invention to provide an endophyte which can produce ergovaline and some ergoline and ergolene compounds at the base of the tall fescue leaf sheaths and in the crown of the plant but only in a manner such that the usual concentration in herbage as generally consumed by grazing animals in common farming practice is less than a practical threshold toxicity level.

For the purposes of this specification "crown" is defined as that area of a grass plant which is generally less than 2 cm above soil level and excludes the roots of the grass, but includes the base of tillers and lateral meristem growing points for new vegetative tillers.

It is a further object of the invention to provide an endophyte which can produce lolines in amounts which are considered to be partially or substantially effective in deterring some insect pests from feeding on plants.

It is a further object of the invention to provide an endophyte which does not produce detectable levels of lolitrems and are not observably tremorgenic.

It is a still further object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

According to one aspect of the present invention there is provided an endophyte of *Neotyphodium coenophialum* species, selected from the group consisting of: AR512; AR513; AR514; AR517; AR521; AR522; AR524; AR525; AR535; AR539; and combinations thereof; AR512; AR513; AR514; AR517; AR521; AR522; AR524; AR525; AR535, AR539 being cultures deposited on 2 Oct. 2002 at the Australian Government Analytical Laboratories (AGAL) with accession numbers: NM02/31935; NM02/31936; NM02/31937; NM02/31938; NM02/31939; NM02/31940; NM02/31941; NM02/31942; NM02/31943; NM02/31944;

characterised in that, in combination with a host grass, said endophyte does not cause symptoms of toxicosis in animals;

and further characterised in that the endophyte retains sufficient levels of at least two alkaloids selected from the group consisting of: agroclavine; setoclavine; isosetoclavine; and combinations thereof, that protect the host grass from pests or abiotic stresses or both;

and further characterised in that the host grass is artificially inoculated with the endophyte.

According to a further aspect of the present invention there is provided an endophyte culture of *Neotyphodium coenophialum* species, selected from the group consisting of: AR512; AR513; AR514; AR517; AR521; AR522; AR524; AR525; AR535; AR539; and combinations thereof; AR512; AR513; AR514; AR517; AR521; AR522; AR524; AR525; AR535, AR539 being cultures deposited on 2 Oct. 2002 at the Australian Government Analytical Laboratories (AGAL) with accession numbers: NM02/31935; NM02/31936; NM02/31937; NM02/31938; NM02/31939; NM02/31940; NM02/31941; NM02/31942; NM02/31943; NM02/31944;

characterised in that, in combination with a host grass, said endophyte culture does not cause symptoms of toxicosis in animals;

and further characterised in that the endophyte culture retains sufficient levels of at least two alkaloids selected from the group consisting of: agroclavine; setoclavine; isosetoclavine; and combinations thereof, that protect the host grass from pests or abiotic stresses or both;

and further characterised in that the host grass is artificially inoculated with the endophyte culture.

Preferably, the toxicosis which is avoided is fescue toxicosis. Most preferably the toxicosis is caused by an ergovaline toxin.

Preferably, the level of ergovaline in the present invention is less than 0.4 ppm in dry matter in herbage consumed by grazing animals. More preferably, the level of ergovaline is less than 0.4 ppm in dry matter in herbage, other than the crown of the host grass plant, consumed by grazing animals.

Preferably, the abiotic stress is a water deficit.

Preferably, the endophyte culture, if used, is an axenic culture.

Preferably, the endophyte or endophyte culture produces less than 0.2 ppm ergovaline in dry matter of whole herbage when infected into host grass.

According to a further aspect of the present invention there is provided a combination of the endophyte as described above, and a host grass.

According to another aspect of the present invention there is provided a combination of the endophyte culture as described above, and a host grass.

Preferably, the combination, substantially as described above, is achieved by modification of host grass infected with the endophyte or endophyte culture by methods selected from the group consisting of: breeding; crossing; hybridisation; genetic modification; and combinations thereof.

Preferably, the host grass used in the combination described above is selected from the group consisting of: tall fescue grass cultivar, ryegrass culivar, meadow fescue cultivar, and combinations thereof.

According to a further aspect of the present invention the host grass is a Pooideae grass.

According to a further aspect of the present invention there is provided a combination of endophyte or endophyte culture, as described above, and a host grass wherein the combination produces isosetoclavine and setoclavine at a rate of greater than 0.5 ppm each of dry matter in the host grass plant crowns. Preferably also, the combination produces less than 0.2 ppm of dry matter of ergovaline in whole heritage.

According to a further aspect of the present invention there is provided a combination of endophyte as described above and a host grass, wherein the combination has features selected from the group consisting of: enhancement of pest protection, resistance to insects, pasture persistence, and combinations thereof.

According to a further aspect of the present invention there is provided a combination as described above and a host grass, wherein the combination has the features of enhancement of grazing animal growth and increased animal productivity relative to grass infected with known endophytes capable of inducing fescue toxicosis.

According to a further aspect of the present invention there is provided a combination as described above and a host grass wherein the pest to which increased resistance is conferred on the host grass is selected from the group consisting of: lesion nematode, root aphid, corn flea beetle, and combinations thereof.

According to a further aspect of the present invention there is provided seeds of a host grass infected with the endophyte substantially as described above.

According to yet a further aspect of the present invention there is provided seeds of a host grass infected with endophyte culture as described above.

The invention is the combination of examples of a class of *Neotyphodium coenophlalum* endophyte and improved grass cultivars by artificial inoculation to produce host grasses which do not cause symptoms of toxicosis by way of the ergovaline toxin, but which retain sufficient levels of other alkaloids (for example: agroclavine, setoclavine and/or isosetoclavine) to individually or in combination continue to protect the host grass from pests or abiotic stresses (such as water deficit) or both.

The inventon has been achieved by understanding the biology of endophytes of temperate climate grasses, isolating selected endophytes of interest, inoculating the endophytes into surface-sterilised seedlings of grasses, exemplified by improved tall fescue or perennial ryegrass cultivar lines, re-evaluating alkaloid production, multiplying seed, evaluating for agronomic factors, testing for animal production, evaluating for any evidence of animal disorders such as fescue toxicosis, staggers, hyperthermia, or prolactin hormone depression and testing for invertebrate pest protection.

The invention consists of the foregoing and also envisages constructions of which the following are examples.

BEST MODES FOR CARRYING OUT THE INVENTION

Culture Conditions and Description

All endophytes of this invention are strains from collections of seed of tall fescue originally sourced from the Claviplus class. Seed from various tall fescue collections were examined for the presence of endophyte by seed squash technique. A selection of plants for each seed sample, where an endophyte was shown to be present, were grown for a few weeks in glasshouse conditions and re-tested for endophyte presence in their leaf sheaths.

The endophytes from plants with chemotypes of interest were isolated and grown in culture according to the method of Latch and Christensen (1985). The endophytes of this invention are held in a culture collection or in cloned plants at the Grasslands site of AgResearch Ltd in Palmerston North, New Zealand. The cultures are also deposited at the Australian Government Analytical Laboratories in Sydney, Australia.

The endophyte cultures were deposited with the Australian Government Analytical Laboratories (AGAL), New South Wales Regional Laboratory, 1, Suakin Street Pymble NSW 2073, Australia, on Oct. 2, 2002, under the terms of the Budapest Treaty on the International Recognition of the Deposit of Microorganisms for the Purposes of Patent Procedure. They were assigned the following numbers: NM02/31935 (AR512); NM02/31936 (AR513); NM02/31937 (AR514); NM02/31938 (AR517); NM02/31939 (AR521); NM02/31940 (AR522); NM02/31941 (AR524); NM02/31942 (AR525); NM02/31943 (AR535); and NM02/31944 (AR539). All strains of endophyte of this invention accommodates within a single sub-grouping of the species *Neotyphodium coenophialum*. The isolates, when grown on potato dextrose agar at 22° C., are slow-growing (radial growth approximately 0.1-0.3 mm per day) with colonies typically white and cottony. Conidia have been observed at variable rates of production near the margins.

Inoculations

Axenic cultures of endophytes AR512, AR513, AR514, AR517, AR521, AR522, AR524, AR525, AR535, and AR539 as examples of this invention, were successfully inoculated (Latch and Christensen, 1985) into seedlings grown from surfaced sterilised seed of the tall fescue cultivar Kentucky 31. Endophytes AR514, AR524, and AR525 were also infected into other cultivars such as, for example Grasslands Flecha, Jesup Improved, Georgia 5 and various experimental lines, generally with a satisfactory success rate well in excess of 5% of attempts. No complete failures to infect tall fescue were observed with the endophytes of this invention.

A typical meadow fescue cultivar (Ensign) was successfully inoculated with endophyte AR512. Similarly a typical perennial ryegrass test line (GA66) was successfully inoculated with endophytes AR514 and AR525 for further examination with the chemotype characteristics of the combinations similar as for when infecting tall fescue, but generally with lower levels of alkaloid accumulation, and with rates of infection of the order of 1% to 5% of attempts.

Seed has been successfully produced from infected plants containing endophytes of this invention under routine seed production conditions with relatively high and useful rates of endophyte infection.

Chemotype Identification

Basal parts of endophyte-infected tillers were freeze dried, sometimes milled, and extracted and analysed qualitatively for the presence of ergovaline by high performance liquid chromatography (HPLC) as set out below. Those indicating ergovaline less than approximately 0.2 ppm of dry matter were further analysed for the production of peramine at rates greater than about 2 ppm of dry matter. The endophytes from such selections were isolated, classified by culture attributes, and generally re-inoculated into seedlings of endophyte-free tall fescue, cultivar Kentucky 31, as a typical improved pasture host for comparative purposes. Samples from such plants at various stages of growth were analysed in more detail for alkaloid production, including for the production of tremorgenic lolitrems typical of *N. lolli* infection and lolines typical of *N. coenophialum*.

The expression of alkaloid production of endophyte-infected tall fescue, using endophytes selected from tall fescue sources, was observed to fall broadly into three groups. The most numerous group produce both ergovaline and peramine at levels often well in excess of 1 ppm in the basal tiller material. Such endophytes are likely to be associated with fescue toxicosis of grazing animals if present at high rates of infection in forage.

A second chemotype group produced peramine and lolines, but no detectable trace of ergovaline. Endophytes typical of this group have been developed for commercial application (Bouton, 2000; Bouton et al., 2002, U.S. Pat. No. 6,111,170).

A third group, of this invention, which have low levels and a characteristic distribution within plants of ergovaline, are discussed below. They are further characterised by the presence of peramine in herbage generally well in excess of 1 ppm, and the presence of lolines in herbage in amounts within ranges typical of *N. coenophialum* infection. In the course of chromatographic analysis for ergovaline the presence of other compounds with UV and fluorescence spectral properties typical of ergolene derivatives (i.e. fluorescent "ergot alkaloids") were observed, notably in the basal portions of tillers, crowns, and seed of tall fescue plants infected with this group of endophytes. These compounds are also discussed below.

Lolines (N-formylloline, N-acetylloline, and N-acetylnorloline, in order of usual observed abundance) were detected by capillary gas chromatography in extracts of tall fescue and meadow fescue plants infected with the endophytes of this invention in amounts more or less comparable to that observed in comparable tall fescue plants infected with common *N. coenophialum*. The methods used were minor modifications of the method of Yates et al., (1990).

Lolitrems were not detected by chromatographic analysis in any tall fescue infected with endophytes of this invention. The possible effects of lolitrems were not further directly considered, other than by observation of lambs grazing pastures containing endophyte AR514 for signs of tremors.

Ergot Alkaloid Levels and Identification of New Alkaloids

Ergovaline concentration was measured by HPLC with fluorescence detection. Typically, a sample of approximately 50 mg of milled (1 mm mesh), freeze-dried endophyte-infected tissue from the lower 3 to 5 cm of tillers from mature vegetative plants (basal tiller material predominantly consisting of leaf sheaths) was extracted with 1 ml of a mixture of equal parts of propan-2-ol and water containing also 1% lactic acid. The extraction continued for one hour at ambient temperature with gentle mixing. An internal standard of added ergotamine tartrate (c. 1 µg per sample) was used for quantitative comparisons.

Following brief centrifugation, a sample of the clarified extract solution was taken for HPLC using a reverse phase column (typically Prodigy 150×4.6 mm, 5 µm silica ODS (3), Phenomenex, Calif., USA), with elution at 1 ml per minute and a solvent gradient of acetonitrile and 100 mM aqueous ammonium acetate by volume starting at 27.5% acetonitrile and progressing in linear stages to 35% at 20 min, 50% at 35 min, 60% at 40 min and 75% at 50 min.

Naturally fluorescent ergolene compounds including ergovaline (and Rs isomer ergovalinine), the internal standard ergotamine (and its isomer ergotaminine partially formed during extraction) and the compounds observed in the earlier section of the chromatograms were detected by using UV excitation at 310 nm and emission at 410 nm. Ergovaline, its isomer ergovalinine, added ergotamine internal standard and its isomer ergotaminine elute at approximately 22, 36, 30 and 42 minutes respectively. The minimum detection level for routine analysis of ergovaline (combined amounts with isomer ergovalinine) is approximately 0.05 ppm of dry matter.

During the course of examining examples of tall fescue infected with endophytes of this invention for ergovaline, other ergolene derivatives were observed to be present in a pattern not previous recognised. Compounds eluting at approximately 6.5 minutes (compound A) and 8.0 minutes (compound B) are characteristically both present in endophyte-infected basal tiller and crown material of this invention. These compounds have been identified as isosetoclavine and setoclavine respectively, as follows.

Fractions enriched in compounds A and B were prepared from a methanol-1% aqueous acetic acid (4:1) extract of bulked freeze dried and milled lower sheath of tillers containing endophytes AR514 and AR524 (pre-extracted with hexane). The extract was fractionated by sequential reverse-phase flash chromatography on octadecyl-functionalised silica gel (Aldrich) with acidic (methanol-1% aqueous acetic acid) and neutral (methanol-water) step gradients, and normal-phase flash chromatography on silica gel (silica gel 60, 40-63 µ, Merck) with an ethyl acetate—methanol step gradient The characteristic fluorescence and the UV absorption spectra and electrospray ionisaton (ESI) mass spectral data for compounds A and B obtained by HPLC analysis of enriched fractions using variations of HPLC separation conditions and detectors (Shimadzu LC-MS instrument QP-5050 with SPD-10AVP UV diode array and RF-10A fluorescence spectral detectors), together with comparative data with standards establish these compounds are setoclavines (isosetoclavine and setoclavine respectively). Both compounds show strong fluorescence peaks in the HPLC ($\lambda_{Ex}$ 310 nm $\lambda_{Em}$ 410 nm). The UV spectra are characterised by maximum absorbances at 307 nm and 312 nm respectively and for both compounds the positive ion ESI mass spectrum shows a base peak at m/z=237 ($MH^+$-$H_2O$) and an $MH^+$ ion at m/z=255. Compound B co-eluted with a sample of reference setoclavine provided by Dr Miroslav Flieger, Institute of Microbiology Academy of Sciences of the Czech Republic. Compounds A and B were identical by HPLC, and spectral properties to isosetoclavine (compound A) and setoclavine (compound B) obtained by chemical oxidation of agroclavine by a standard procedure. The presence of isosetoclavine and setoclavine has not been previously reported in endophyte infected grasses although they have been reported as oxidation products of agroclavine in other plant systems (review by Kren, 1999).

The same extracts were also shown to contain agroclavine by electrospray LC-MS, with an ESI mass spectrum ion attributed to $MH^+$ at m/z=239 eluting at the same time and with essentially the same UV spectrum as authentic agroclavine.

Table 1 summarises alkaloid analysis results of specified plant parts of tall fescue infected with the endophytes and usually grown under temperate summer season conditions, generally in comparative test cultivar Kentucky 31. For consideration of ergot alkaloid production in the crown and basal tiller, comparison is also made to tall fescue infected with endophytes AR501 and AR542 which consistently do not appear to produce any ergovaline or setoclavines.

TABLE 1

Examples and typical ranges or scores of alkaloids observed in specified plant parts

| Sample (cultivar & endophyte) | Part of plant | Ergovaline (ppm DM) | Compounds A & B |
|---|---|---|---|
| Jesup EI | Whole herbage | 0.4-1.2 | ND |
| Jesup EI | Sheath | 2.5 | |
| Manawatu RS EI | Sheath | 7.1-15.7 | |
| Kentucky 31 EI | Whole Herbage | 1.8-3.0 | ND |
| Kentucky 31 EI | Leaf blade | 0.3-1.8 | ND |
| Kentucky 31 EI | Sheath | 2.9-16.2 | |
| Kentucky 31 AR501 | Crown | <0.1$^{ND}$ | * |
| Kentucky 31 AR514 | Whole herbage | <0.1 | * |
| Kentucky 31 AR514 | Crown | 0.1-0.6 | ** |
| Kentucky 31 AR514 | Immature heads | <0.1-0.2 | * |
| Kentucky 31 AR522 | Stem & sheath | 0.1-0.2 | * |
| Kentucky 31 AR522 | Crown | 3.4-6.1 | *** |
| Kentucky 31 AR524 | Crown | 0.3-0.6 | ** |
| Kentucky 31 AR524 | Immature heads | <0.1 | * |
| Kentucky 31 AR525 | Whole herbage | <0.1 | ND |
| Kentucky 31 AR525 | Crown | 0.7-1.0 | *** |
| Kentucky 31 AR525 | Immature heads | <0.1 | * |
| Kentucky 31 AR525 | Stem, sheath & heads | <0.1 | * |
| Kentucky 31 AR535 | Crown | 0.4-0.7 | *** |
| Kentucky 31 AR535 | Stem, sheath & heads | <0.1 | ** |
| Kentucky 31 AR542 | Crown | <0.1 | ND |
| Kentucky 31 AR542 | Sheath | <0.1 | ND |

Compound A = isosetoclavine
Compound B = setoclavine
ND = not detected, detection limit of 0.1 ppm DM for ergovaline
* = possible trace or low level
 and * = score of relative abundance observed
EI = infected with common toxic or wild type endophyte Genotype Characterization of Endophyte All endophytes discussed above are characterised by DNA "fingerprinting" (selected polymorphic microsatellite loci and/or Arbitrary Fragment Length Polymorphisms (AFLP) technique) as belonging to a sub-group of *Neotyphodium coenophialum*.

Samples of about 50 mg fresh or 15 mg dry basal tiller were used for the extraction of DNA using FastDNA kit for plants (Bio 101, Vista, California) by procedures recommended with the kit. Alternatively genomic DNA was extracted from cultured endophyte (Moon et al., 1999). Microsatellite PCR amplification was performed using primer pairs labelled with fluorescent dyes, B10.1 (5'-TET)/B10.2 and B11.1 (5'-HEX)/B11.4, as described by Moon et al., (1999). The apparent size of microsatellite PCR fluorescent labelled products was measured relatively to within an estimated 0.3 nucleotide units by capillary electrophoresis using an ABI 3100 Genetic Analyzer with POP6 polymer chemistry in 50 cm capillary arrays and GeneScan-400HD standards (Applied Biosystems Inc., Foster City, Calif.). The apparent sizes of PCR products by this technique (adjusted by subtracting a unit where an adenine nucleotide appears to have been terminally added) are set out in Table 2.

Table 2 shows that the endophytes of this invention can be distinguished from other groups of *Neotyphodium* endophytes by the number of alleles observed and the apparent sizes of such alleles. Thus all strains of this invention share a B11 allele of size c. 128 base pairs and a second B11 allele within the size range c. 192 to 200 bp. They also share with other *N. coenophialum* strains up to three B10 alleles within the range c.154 to 185 bp.

The presence of three alleles for the endophytes of this invention for the B10 locus is consistent with evidence for *N. coenophialum* as a hybrid endophyte derived from three different *Epichloë* source species (Tsai et al., 1994).

Analysis by AFLP (Griffiths et al., 1999) also confirmed that endophyte examples AR514, AR525 and AR535 of this invention are from a sub-group which can be distinguished from other *N. coenophialum* endophytes outside this sub-group by one or more polymorphic differences, but not many differences, from within more than 200 AFLP bands observed to be polymorphic for the genera *Neotyphodium* and *Epichloë*.

Safe Grazing with Endophyte in Tall Fescue Cultivar Kentucky 31

Pastures of tall fescue infected with examples of the endophytes of this invention do not induce typical fescue toxicosis in grazing animals. Table 3 shows growth rate of lambs in a trial conducted at Eatonton, Ga., USA for two seasons (21 Apr.-30 Jun. 1997, 2 Apr.-2 Jul. 1998). The growth of lambs on a pasture of Kentucky 31 tall fescue infected with endophyte strain AR514 was essentially the same growth as on equivalent endophyte-free pasture and significantly better than growth on naturally endophyte-infected pasture using the comparable Jesup cultivar. The wild type endophyte infection significantly reduced live weight gain ($P<0.05$) and increased mean body (rectal) temperature.

Gross depression of prolactin in blood is another symptom of fescue toxicosis. Endophyte strain AR514 did not cause a depression of prolactin whereas with the wild type endophyte prolactin was grossly reduced.

Overall, the performance of lambs grazing on AR514 pasture was similar to that on the endophyte-free pasture. No tremors or "ryegrass staggers" symptoms were observed.

TABLE 2

Apparent size of B10 and B11 microsatellite PCR products.

| | B10 locus | | B11 locus | |
|---|---|---|---|---|
| Source material | No of alleles | Allele sizes (bp) | No of alleles | Allele sizes (bp) |
| *N. coenophialum*, wild type, Australian C1, coB isozymes | 3 | 160.4, 169.6, 184.2 | 2 | 147.9, 192.2 |
| *N. coenophialum*, wild type, NZ Tindall's, coB isozymes | 2 | 160.4, 169.4 | 2 | 147.9, 192.2 |
| *N. coenophialum*, wild type, NZ RS2 & NZ RS6 | 3 | 160.3, 169.3, 184.2 | 2 | 147.8, 192.0 |
| *N. coenophialum*, AR542 | 2 | 160.5, 169.6 | 2 | 180.4, 192.2 |
| *Neotyphodium* sp., FaTG-3 strain AR501 | 2 | 169.5, 178.7 | 1 | 127.9 |
| *Neotyphodium* sp., FaTG-3 strain AR506 | 2 | 169.6, 178.7 | 1 | 127.8 |
| AR539 | 3 | 154.6, 172.5, 178.3 | 2 | 127.9, 192.2 |
| AR513 | 3 | 157.7, 160.5, 178.4 | 2 | 128.0, 192.2 |
| AR525 | 3 | 157.7, 160.4, 178.3 | 2 | 128.0, 192.2 |
| AR517 | 3 | 163.4, 172.5, 178.2 | 2 | 128.0, 192.1 |
| AR521 | 3 | 163.3, 172.5, 178.2 | 2 | 127.9, 192.1 |
| AR512 | 3 | 172.6, 178.5, 181.5 | 2 | 128.0, 192.2 |
| AR514 | 3 | 157.8, 160.6, 178.4 | 2 | 128.0, 196.2 |
| AR522 | 3 | 157.7, 160.5, 178.3 | 2 | 128.0, 200.1 |
| AR524 | 3 | 157.7, 160.5, 178.3 | 2 | 127.9, 200.2 |
| AR535 | 3 | 157.7, 160.5, 178.3 | 2 | 128.0, 200.1 |

TABLE 3

Performance of lambs grazing endophyte infected and endophyte free pasture.

| | | Endophyte treatment | | |
|---|---|---|---|---|
| | Year | AR514 (in Kentucky 31) | Jesup EF* | Jesup EI* |
| Live weight gain (g/hd/d) | 1997 | 103 a** | 102 a | 67 b |
| | 1998 | 93 a | 102 a | 57 b |
| Body temperature (° C.) | 1997 | 39.8 a | 39.8 a | 40.1 b |
| Blood prolactin (ng/ml) | 1997 | 414 a | 400 a | Not detectable (b) |
| | 1998 | 550 a | 150 a | <0.5 b |

*EF = endophyte free; EI = infected with common toxic or wild type endophyte.
**Treatments with no letter in common are significantly different (P < 0.05).

Endophytes and Resistance to Lesion Nematodes

In some environments, notably sandy soils with relatively warm and humid climates, nematode may cause significant damage to tall fescue root systems thus affecting the persistence of the grass in the pasture. A greenhouse trial with three plants and nine replicates per treatment has demonstrated that endophyte infection may confer resistance to lesion nematodes, *Pratylenchus* spp. In a greenhouse experiment nematode reproduction was investigated with two tall fescue cultivars infected with various endophytes or endophyte free.

Table 4 indicates that an endophyte of this invention, AR514, confers partial resistance to lesion nematodes to a greater degree than endophyte-free plants (EF) or two endophytes lacking production of ergovaline (AR542 & AR584) although not to the same degree as the common endophyte (EI) of the cultivars.

TABLE 4

Endophyte effect on lesion nematode numbers

| Fescue cultivar | Endophyte | | | | |
|---|---|---|---|---|---|
| | EF* | AR542 | AR584 | AR514 | EI* |
| GA 5 | 146 | 149 | 101 | — | 19 |
| Jesup | 147 | 88 | 120 | 69 | 30 |
| Mean | 146 a** | 118 ab | 111 ab | 69 b | 24 c |
| Relative to EF = 100 | 100 a | 81 ab | 76 ab | 47 b | 16 c |

*EF = endophyte free; EI = infected with common toxic or wild type endophyte.
**Treatments with no letter in common are significantly different (P < 0.05).

Endophytes Confer Resistance to Root Aphid

Endophyte infection is known to affect infestation of grasses by aphids. Table 5 compares treatments of fourteen plants each of tall fescue cultivar Kentucky 31 for mean numbers of root aphids wherein AR514 infection is shown to confer considerable protection in comparison with another endophyte-infected set of plants or endophyte free plants.

TABLE 5

Log number of root aphid per 10 ml sub-sample in Kentucky 31 tall fescue.

| Endophyte treatment | No. root aphid | No. root aphid/gm root |
|---|---|---|
| Endophyte Free | 4.043 a* | 2.055 a |
| AR542 | 1.710 b | 0.473 b |
| AR514 | 0.765 c | 0.095 c |

*Treatments with no letter in common are significantly different (P < 0.01)

Endophytes Confer Deterrence to Corn Flea Beetle

Tall fescue Kentucky 31 leaves infected with examples of the endophytes of this invention (E+) and also leaves infected with wild type toxic endophyte were compared with endophyte free (EF) material using the corn flea beetle *Chaetocnema pulicaria* in a feeding preference test experiment. Endophytes AR512, AR513, AR514, AR524 and AR525 all conferred resistance or feeding deterrence similar to that of leaves infected with the wild type toxic endophyte. The mean of feeding scores for the examples of this invention were E+=0.4 as against EF=2.8 (P<0.001) on a scale of 0 to 3 (where 0 is no feeding and 3 is extensive feeding). Score counts of feeding scars (E+=2.2, EF=27.8, mean of the total number of scars across 3 transects per leaf blade) and of faecal pellets (E+=9.2, EF=75.8, mean number of faecal pellets on each blade) were also highly significantly different with those for E+ closely comparable to those of toxic wild type endophyte of Kentucky 31.

A similar single preference test with endophyte AR512 infected into meadow fescue cultivar Ensign demonstrated an even more extreme preference effect with feeding scores of E+=0.0, EF=3.0, feeding scars score counts E+=0, EF=33, and faecal pellets E+=3, EF=50.

Aspects of the present invention have been described by way of example only and it should be appreciated that modifications and additions may be made thereto without departing from the scope thereof.

REFERENCES

Blank, C. A.; Gwinn, K. D. 1992: Soilborne seedling diseases of tall fescue: Influence of the endophyte *Acremonium coenophialum*. Phytopathology 82: 1089.

Bouton, J. H. 2000: The use of endophyte fungi for pasture improvement in the USA. In Proceedings of The Grassland Conference 2000, 4th International *Neotyphodium*/Grass Interactions Symposium. Eds. Paul, V. H.; Dapprich, P. D. Universtät, Paderborn, pp 163-168.

Bouton, J. H.; Latch, G. C. M.; Hill, N. S.; Hoveland, C. S.; McCann, M. A.; Watson, R. H.; Parish, J. H.; Hawkins, L. L; Thompson, F. N. 2002: Re-infection of tall fescue cultivars with non-ergot alkaloid-producing endophytes. Agronomy Journal 94: 567-574.

Elberson, H. W.; West, C. P. 1996: Growth and water relations of field grown tall fescue as influenced by drought and endophyte. Grass and Forage Science 51:333-342.

Fletcher, L, R,; Easton, H. S.; 2000: Using Endophytes for Pasture Improvement in New Zealand. In Proceedings of The Grassland Conference 2000, 4th International *Neotyphodium*/Grass Interactions Symposium. Eds. Paul, V. H.; Dapprich, P. D. Universtät, Paderborn, pp 149-162.

Fletcher, L R.; Sutherland, B. L.; Fletcher, C. G. 1999: The impact of endophyte on the health and productivity of sheep grazing ryegrass-based pastures. In Ryegrass endophyte: an essential New Zealand symbiosis. Grassland Research and Practice Series No. 7, pp 11-17.

Gadberry, M. S.; Denard, T. M.; Spiers, D. E.; Piper, E. L.; 1997: Ovis airies: A model for studying the effects of fescue toxins on animal performance in a heat-stress environment. In *Neotyphodium*/Grass Interactions, Eds. Bacon, C. W.; Hill, N. S. Plenum Press, New York, pp 429-431.

Griffiths, A.; Moon, C.; Tapper, B.; Christensen, M. 1999: Non-radioactive AFLP fingerprinting for detection of genetic variation in *Epichloë/Neotyphodium* endophytes. Proceedings of the 11th Australian Plant Breeding Conference.

Hill, N. S.; Thompson, F. N.; Studemann, J A.; Rottinghaus, G. W.; Ju, H. J.; Dawe, D. L.; Hiatt, E. E. 2001: Ergot alkaloid transport across ruminant gastric tissues. Journal of Animal Science 79: 542-549

Kren, V.1999: Biotransformations of ergot alkaloids. In Ergot the genus *Claviceps*. Eds. Kren, V.; Cvak, L. Harwood Academic, Amsterdam, p. 230

Latch, G. C. M.; Christensen, M. J. 1985: Artificial infection of grasses with endophytes. Annals of Applied Biology 107:17-24.

Leuchtmann, A. 1997: Ecological diversity in *Neotyphodium*-infected grasses as influenced by host and fungus characteristics. In *Neotyphodium*/Grass Interactions, Eds. Bacon, C. W.; Hill, N. S. Plenum Press, New York, pp 93-108.

Moon, C. D.; Tapper, B. A.; Scott, D. B. 1999: Identification of *Epichloë* endophytes in planta by a microsatellite-based PCR fingerprinting assay with automated analysis. Applied and Environmental Microbiology 65: 1268-1279.

Oliver, J. W. 1997: Physiological manifestations of endophyte toxicosis in ruminant and laboratory species. In *Neotyphodium*/Grass Interactions, Eds. Bacon, C. W.; Hill, N.S Plenum Press, New York, pp 311-346.

Rottinghaus, G. E.; Garner, G. B.; Comell; C. N.; Ellis; J. L. 1991; HPLC method of quantitating ergovaline in endophyte-infected tall fescue: Seasonal variation of ergovaline levels in stems with leaf sheaths, leaf blades and seed heads. Journal of Agricultural and Food Chemistry 191: 112-115.

Rowan, D. D.; Hunt, M. B.; Gaynor, D. L. 1986: Peramine, a novel insect feeding deterrent from ryegrass infected with the endophyte Acremonium loliae. J. Chem. Soc. Chem. Commun. 1986. 935-936.

Rowan, D. D.; Latch, G. C. M. 1994: Utilization of endophyte-infected perennial ryegrasses for increased insect resistance. In Biotechnology of endophyte fungi in grasses. Eds. Bacon, C. W. White, J. CRC Press, pp 169-183.

Siegel, M. R.; Latch, G. C. M.; Bush, L. P.; Fannin, F. F.; Rowan, D. D.; Tapper, B. A.; Bacon, C. W.; Johnson, M. C. 1990: Fungal endophyte-infected grasses: alkaloid accumulaton and aphid response. Journal of Chemical Ecology 16: 3301-3315.

Stuedemann, J. A.; Hoveland. C. 1988: Fescue endophyte: History and impact on animal agriculture. Journal of Production Agriculture 1: 39-44.

Tapper, B. A.; Latch, G. C. M. 1999: Selection against toxin production in endophyte-infected perennial ryegrass. In Ryegrass endophyte: an essential New Zealand symbiosis. Grassland Research and Practice Series No. 7, pp 107-111.

Tor-Agbidye, J.; Blythe, L. L.; Craig, A. M. 2001: Correlation of endophyte toxins (ergovaline and lolitrem B) with clinical disease: fescue foot and perennial ryegrass staggers. Veterinary and Human Toxicology 43: 140-146.

Tsal, H. F.; Liu, J. S.; Staben, C.; Christensen, M. J.; Latch, G. C.; Siegel, M. R.; Schardl, C. L. 1994: Evolutionary diversification of fungal endophytes of tall fescue grass by hybridization with *Epichloë* species. Proceedings of the National Academy of Science USA 91: 2542-2546.

Yates, S. G.; Petroski, R. J.; Powell, R. G. 1990: Analysis of loline alkaloids in endophyte-infected tall fescue by capillary gas chromatography. Journal of Agricultural and Food Chemistry 38: 182-185.

What we claim is:

1. A biologically pure culture of an endophyte of the *Neotyphodium coenophialum* species, selected from the group consisting of: AR512; AR513; AR514; AR517; AR521; AR522; AR524; AR525; AR535; AR539; and combinations thereof; AR512; AR513; AR514; AR517; AR521; AR522; AR524; AR525; AR535, AR539 being cultures deposited on 2 Oct. 2002 at the Australian Government Analytical Laboratories (AGAL) with accession numbers: NM02/31935; NM02/31936; NM02/31937; NM02/31938; NM02/31939; NM02/31940; NM02/31941; NM02/31 942; NM02/31 943; NM02/3 1944, respectively;

characterised in that when the endophyte is combined with a host grass, the endophyte does not produce alkaloid compounds at levels associated with toxicosis in animals;

and further characterised in that when the endophyte is combined with a host grass, the endophyte produces at least two clavine alkaloids selected from the group consisting of: agroclavine; setoclavine; isosetoclavine; and combinations thereof.

2. The endophyte culture as claimed in claim 1 characterised in that the endophyte does not produce alkaloid compounds at levels associated with fescue toxicosis.

3. The endophyte culture as claimed in claim 1 characterised in that the endophyte does not produce ergovaline alkaloid at a level associated with toxicosis.

4. The endophyte culture as claimed in claim 3 characterised in that the endophyte produces a level of ergovaline that is less than 0.4 ppm in dry matter in herbage consumed by grazing animals.

5. The endophyte culture as claimed in claim 3, characterised in that the endophyte produces a level of ergovaline that is less than 0.4 ppm in dry matter in herbage, other than the crown of the host grass, consumed by grazing animals.

6. The endophyte culture as claimed in claim 1 characterised in that the endophyte produces sufficient levels of at least two clavine alkaloids to protect the endophyte and the host grass from pests or abiotic stresses or both.

7. The endophyte culture as claimed in claim 6 characterised in that the clavine alkaloids protect the endophyte and host grass from abiotic stresses wherein the abiotic stress is a water deficit.

8. A biologically pure endophyte culture of *Neotyphodium coenophialum* selected from the group consisting of an endophyte culture deposited with the Australian Government Analytical Laboratories under accession number NM02/31935; NM02/31936; NM02/31937; NM02/31938; NM02/31939; NM02/31940; NM02/31941; NM02/31942; NM02/31943; and NM02/31944.

* * * * *

UNITED STATES PATENT AND TRADEMARK OFFICE
CERTIFICATE OF CORRECTION

PATENT NO. : 7,585,660 B2
APPLICATION NO. : 10/529375
DATED : September 8, 2009
INVENTOR(S) : Christensen et al.

It is certified that error appears in the above-identified patent and that said Letters Patent is hereby corrected as shown below:

On the title page, item (75), line 7, "Lison" should read --Alison--.

Claim 1, column 14, line 15, "NM02/31 942; NM02/31 943;" should read --NM02/31942; NM02/31943--;

line 16, "NM02/3 1944," should read --NM02/31944,--.

Signed and Sealed this

Third Day of November, 2009

David J. Kappos
*Director of the United States Patent and Trademark Office*